United States Patent [19]

Kamen

[11] 4,411,649
[45] Oct. 25, 1983

[54] FLUID FLOW CONTROL SYSTEM

[75] Inventor: Dean L. Kamen, Bedford, N.H.

[73] Assignee: Baxter Travenol Laboratories, Inc., Deerfield, Ill.

[21] Appl. No.: 254,304

[22] Filed: Apr. 15, 1981

Related U.S. Application Data

[63] Continuation-in-part of Ser. No. 56,871, Jul. 12, 1979, abandoned.

[51] Int. Cl.³ ............................................. A61M 5/00
[52] U.S. Cl. ............................ 604/65; 128/DIG. 13; 222/58
[58] Field of Search .................. 128/214 E, DIG. 13; 222/58

[56] References Cited

U.S. PATENT DOCUMENTS

| | | | |
|---|---|---|---|
| 3,329,311 | 7/1967 | Goff et al. | 222/58 |
| 3,623,052 | 11/1971 | Spiller | 340/239 R |
| 3,655,095 | 4/1972 | Kienitz | 128/214 E |
| 3,999,542 | 12/1976 | Shaw | 128/214 E |
| 4,018,362 | 4/1977 | Ubaud | 128/214 E |
| 4,029,094 | 6/1977 | Winicki | 128/214 E |
| 4,098,274 | 7/1978 | Ebling | 128/214 E |
| 4,111,336 | 9/1978 | Ward et al. | 222/58 |
| 4,137,915 | 2/1979 | Kamen | 128/DIG. 13 |
| 4,300,552 | 11/1981 | Cannon | 128/214 E |

FOREIGN PATENT DOCUMENTS 2054200 7/1979 United Kingdom ....... 128/DIG. 13

Primary Examiner—Kyle L. Howell
Assistant Examiner—Karin M. Reichle
Attorney, Agent, or Firm—Bromberg, Sunstein & McGregor

[57] ABSTRACT

In a fluid flow control system a weight detector generates a signal representative of the weight of the fluid in the reservoir. A second signal is generated indicative of the desired fluid weight over time, and a first comparator produces an output indicative of the dissimilarity of the two signals. A programmed drop rate signal is modified by the first comparator's output to produce a desired drop rate signal. A drop detector produces a signal indicative of the actual drop rate. A second comparator is operative upon the desired drop rate signal and the actual drop rate signal to produce an output for operating the flow controller.

1 Claim, 2 Drawing Figures

FLUID FLOW CONTROL SYSTEM

This application is a continuation-in-part of my application Ser. No. 56,871 filed July 12, 1979, now abandoned, which is hereby incorporated herein by reference.

DESCRIPTION

1. Technical Field

The present invention relates generally to fluid flow control systems, particularly those used to control the draining of fluid from a reservoir intravenously into a patient.

2. Background Art

Intravenous fluid control systems are well-known in the prior art. The most primative devices are simply clamps, inserted in physical contact with the fluid line, which are manually adjusted to accomplished the desired flow rate. The invention described in my U.S. Pat. No. 4,137,915 utilizes an electro-mechanical system including an electrically operated clamp, a switch in series with the clamp, and a motor-driven screw and spring arrangement to permit the reservoir to decrease in weight at a rate dependent on the motor speed. Such a system, though a significant advance in the art, requires many moving parts and is limited in accuracy by sensitivity of the switch and mechanical friction and hysteresis.

DISCLOSURE OF INVENTION

It is an object of the present invention to provide a novel fluid flow control system.

It is also an object of the present invention to provide a fluid flow control system having high accuracy and relatively few moving parts.

It is a further object of the present invention to provide a fluid flow control system that can be programmed to deliver fluid to a patient in accordance with any desired schedule.

It is a further object of the present invention to provide a fluid flow control system that utilizes electronic techniques.

These and other objects of the invention are achieved by providing a weight detector, for generating a weight measurement signal that is indicative of the weight of fluid in the reservoir; an adjustable reference generator for generating a weight reference signal that is indicative of the desired rate of decrease in weight of the fluid in the reservoir; and a comparator that produces an output indicative of the dissimilarity between the weight measurement and the weight reference signals. Some embodiments utilize a flow controller, operative upon the fluid line from the reservoir to the patient, that has an input connected so as to receive a signal related to the comparator's output.

In a preferred embodiment, the invention includes a drop counter placed in the line of flow from the reservoir. The drop counter produces an actual drop rate signal. There is also provided a device that generates a programmed drop rate signal. The programmed drop rate signal is modified by the previously described comparator's output to produce a corrected drop rate signal. The actual and the corrected drop rate signals are directed to a second comparator that operates on the flow controller.

BRIEF DESCRIPTION OF THE DRAWINGS

These and other objects and features of the invention will be more readily understood by consideration of the following detailed description taken from the accompanying drawings, in which.

DESCRIPTION OF SPECIFIC EMBODIMENTS

Figure 1:
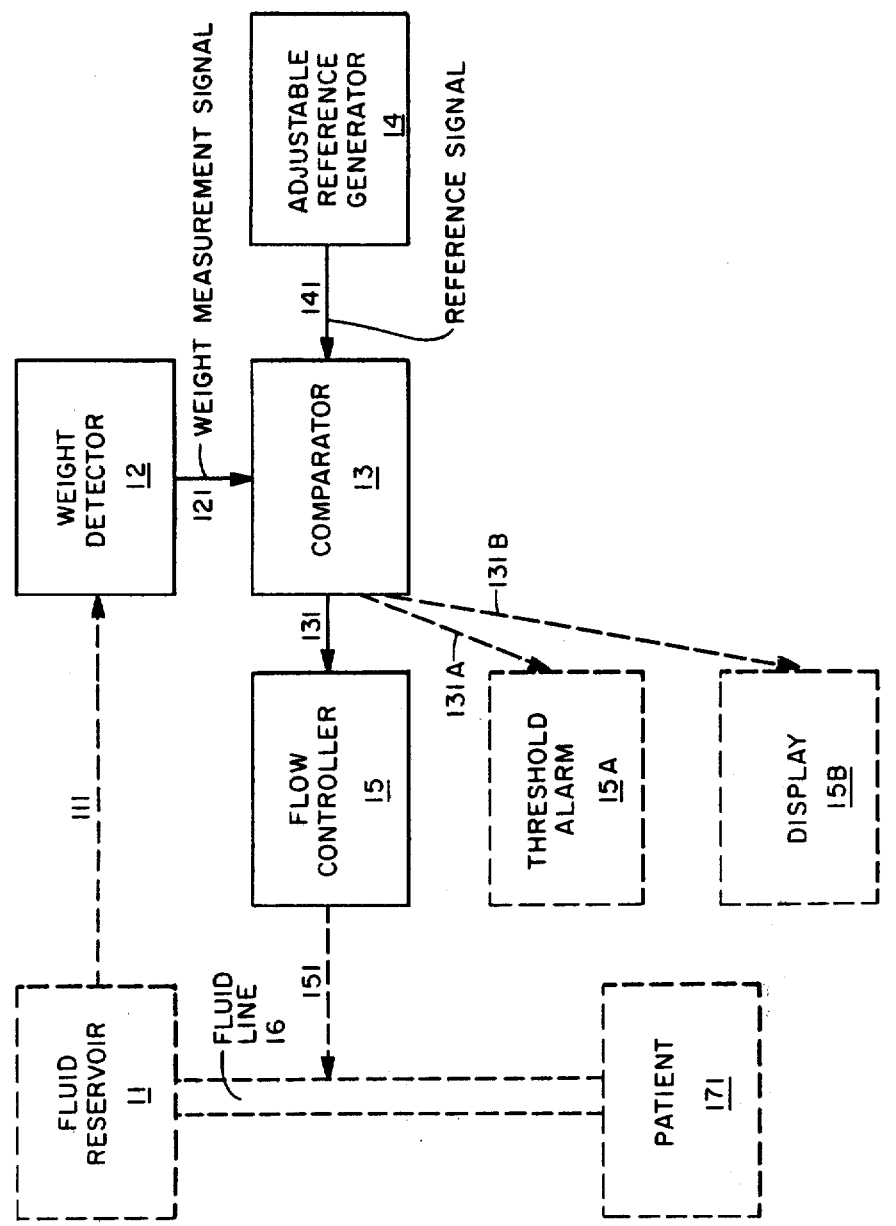
FIG. 1 is a block diagram of a basic fluid flow control system in accordance with the present invention.

Referring to FIG. 1, there is shown a basic embodiment of the invention. The invention operates on a fluid line 16 that is placed between a fluid reservoir 11 and the patient 171. Weight of the fluid reservoir is monitored by weight detector 12. The mechanical relation between the reservoir 11 and the weight detector 12 is indicated by arrow 111. Weight detector 12 may be any electronic device for producing an output as a function of weight of the reservoir, and may, for example, be a strain gauge. As fluid leaves the fluid reservoir 11, the reservoir decreases in weight, and the weight measurement signal, which is an output of weight detector 12 appearing on line 121, will be appropriately modified over time with decrease of the weight in the fluid reservoir. Reference generator 14 provides a reference signal over line 141 that is indicative, at any given time, of the desired value of the weight measurement signal.

The weight measurement and reference signals may be either analog or digital. If such signals are analog, it may be desirable to utilize direct current signals having magnitudes proportional respectively to the measured and desired weights of the fluid reservoir. The reference signal may be programmed to indicate a weight decrease of the fluid reservoir at any desired rate. For example, it may be desired to have the flow in the reservoir cease except during a specified one-hour interval each day. In such a case, for example, the reference signal would then be kept at a constant level except during the specified hour, at which time the reference signal would decrease in accordance with the flow rate desired over that hour; thereafter, the reference signal would again be constant until the next day. The adjustable reference generator may incorporate microprocessors, in accordance with techniques well known in the prior art, to produce such a reference signal.

Still referring to FIG. 1, the reference signal and weight measurement signal are both separate inputs to the comparator 13, which produces an output indicative of the dissimilarity (for example the algebraic difference) between the two signals. The output appears on line 131. It will be apparent, of course, if the weight measurement and reference signals are digital, that the comparator must also be digital. Alternatively, the reference generator 14 may utilize digital processing circuits and appropriate digital-to-analog converters so that the weight measurement and reference signals are both analog. The dissimilarity indicated by the comparator can be a simple "go, no-go" output, an algebraic difference, a phase angle change, or any signal suitable for affecting the flow controller 15. In any event, the comparator output 131 is used to operate on flow controller 15. The controller may be a simple solenoid-operated clamp, which is either opened or closed (and therefore cycling off and on as many times as necessary to produce the appropriate average flow rate), or it may be continuously adjustable to produce a more precisely controlled flow. Because the rate of decrease of the fluid reservoir may be monitored continuously by rate detector 12, the flow controller need only have the means for operating over a suitable range of flow so as to permit operation of the system.

As an alternative, or even in addition, to the flow controller 15 may be a threshold alarm 15A. The alarm emits a detectable signal (such as an audible noise) whenever the signal over line 131A from the comparator 13 is indicative of a difference, between actual cumulative flow (as represented by the weight measurement signal) and desired cumulative flow (as represented by the weight reference signal), that is outside some predetermined set of limits. Also connected to the comparator 13 may be a display 15B for displaying the amount and/or algebraic sign of the foregoing difference. Thus if the threshold alarm 15 indicates that the cumulative flow is too great or too small, the flow can be adjusted appropriately. When used in conjunction with the flow controller 15, the threshold alarm will give warning (i) whenever the flow controller 15 is not functioning properly, or (ii) whenever the fluid reservoir 11 is empty, or (iii) generally whenever blockage or other circumstances undesirably inhibits or increases flow. When used without the flow controller 15, the threshold alarm will give warning under comparable conditions, and alert the user to any circumstance when a manual flow control should be adjusted. In correcting circumstances giving rise to the activation of alarm 15, the user may utilize the display 15B.

Figure 2:
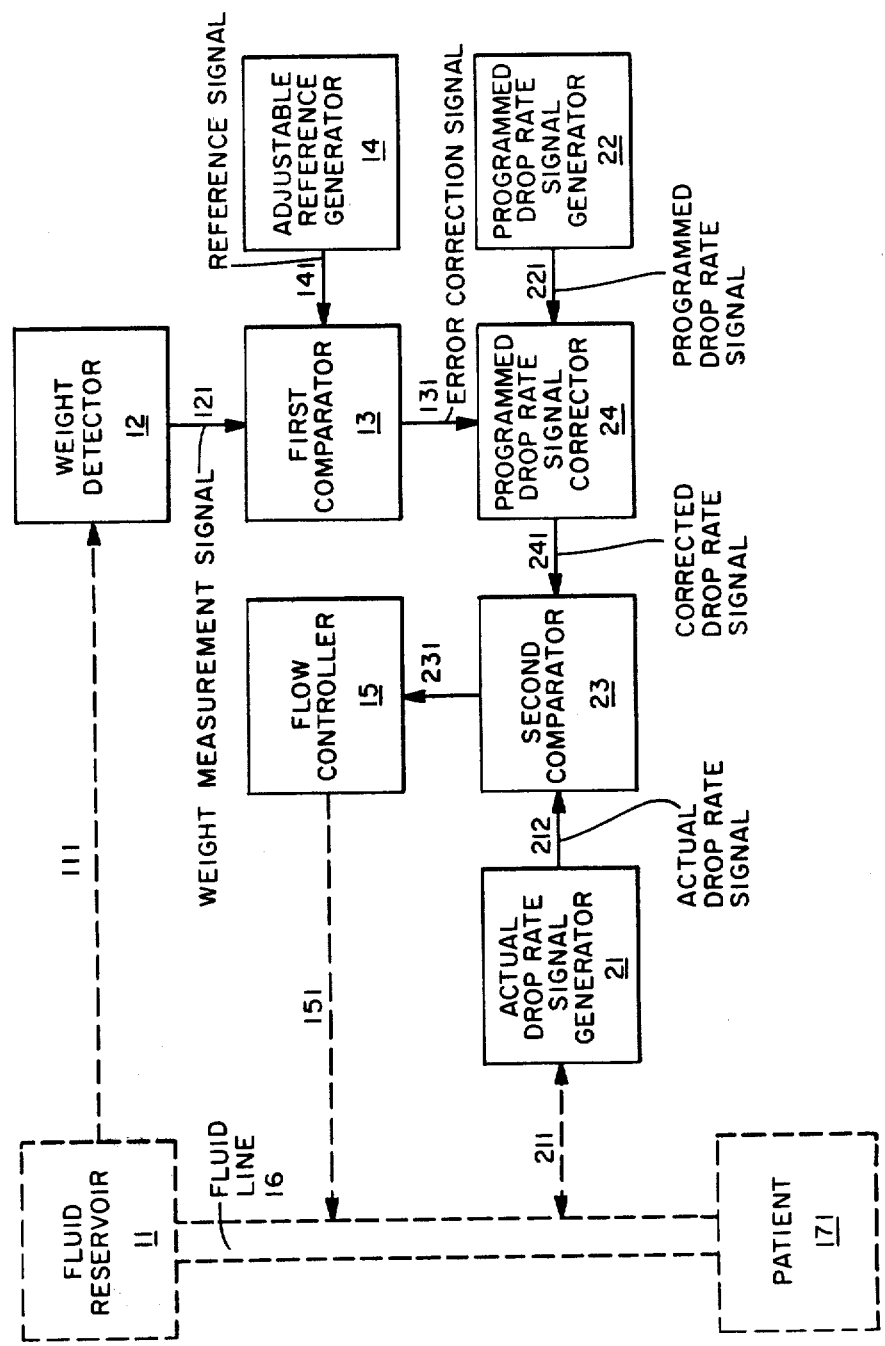
FIG. 2 is a block diagram of a more sophisticated embodiment of the present invention, where a drop counter is utilized.

Referring now to FIG. 2, there is shown a more sophisticated embodiment of the present invention. This embodiment is generally similar to that described with reference to FIG. 1, except that "drop rate" circuitry is used to provide better instantaneous control of flow. There is inserted, in the fluid line 16, an actual drop rate signal generator 21. This signal generator comprises a conventional device for forming the fluid in line 16 into drops and counting the rate at which drops flow through the system. The signal generator 21 has an output on the line 212 that is indicative of the actual drop rate that is measured. This output is called the "actual drop rate signal." The programmed drop rate signal generator 22 has an output on line 221 that is called the "programmed drop rate signal." This signal is an input to the programmed drop rate signal corrector 24, which in turn provides an output, over line 241, called the "corrected drop rate signal." The dissimilarity between the actual and corrected drop rate signals, which are both inputs to the second comparator 23, appears as a function of the output of the second comparator on line 231. This output is used to control the flow controller 15.

Still referring to FIG. 2, initially the programmed drop rate signal, through corrector 24 and second comparator 23, causes operation of the flow controller 15 until the actual drop rate signal is approximately matched by the programmed drop rate signal. However, adjustable reference generator 14 in combination with detector 12, in the manner discussed in connection with FIG. 1, causes an output of the first comparator 13 on line 131 to be indicative of the difference between the actual flow through fluid line 16 and the desired flow. This output is called the error correction signal, and is used as an input to the programmed drop rate signal corrector 24, to produce a corrected drop rate signal on line 241. In this manner, flow through the system on a drop-by-drop basis is controllable by the actual drop rate signal generator 21, the second comparator 23, and the programmed drop rate signal generator 22 and corrector 24; whereas the time-averaged flow is also being monitored by the weight detector 12, the first comparator 13, and the adjustable reference generator 14, which, in combination, keep the instantaneous flow under control so as to produce the appropriate time-averaged behavior of the system.

For many applications, the output of the programmed drop rate signal generator 22 which is produced when the system is first turned on, may be somewhat arbitrary, because within a short time the appropriate error correction signal will appear over line 131, and cause a corrected drop rate signal to appear on line 241. As in the case of generator 14 (as discussed in connection with FIG. 1), the programmed drop rate signal generator 22 and corrector 24 can be made in accordance with designs well known in the prior art. One possible embodiment would be a microprocessor-controlled device that includes a digital-to-analog convertor to permit the output of an analog signal on line 241. Alternatively, the circuitry could be conventional analog circuitry. If more precision is desired when the system is first turned on, the programmed drop rate signal generator 22 can be provided with suitable adjustment to provide a desired initial instantaneous flow rate. The interaction of the drop rate flow measurement signal generator 21 with the fluid line 16 is indicated schematically by double arrow 211.

It will be clear that the error correction signal need not necessarily be provided to the corrector 24 on a continuous basis, so long as drift of the system's accuracy is kept within desired limits; the corrector may be designed to provide a corrected drop rate signal of one specification until a new error correction signal requires the corrector 24 to produce a signal. Thus the weight measurement and reference signals need not necessarily be continuous.

Similarly, the corrected and actual drop rate signals themselves need not necessarily be continuous, since the second comparator 23 and the flow controller 15 may be designed to operate with signals provided at a given clock frequency. Generally, it is desirable to have the clock rate or sample rate of the drop rate circuitry be sufficiently high; otherwise the drop rate circuitry may not significantly improve on the embodiment shown in FIG. 1.

Accordingly, while the invention has been described with particular reference to specific embodiments, it will be understood that it may embodied in a variety of forms diverse from those shown and described without departing from the spirit and scope of the invention as described in the following claims.

What is claimed is:

1. A system for controlling in a desired manner the flow of fluid in a line from a reservoir through a drip chamber to a patient, such system comprising:

first means, for generating a first electrical signal indicative of the weight of the fluid in the reservoir, such first signal hereinafter called the "weight measurement signal";

second means, for generating a second electrical signal indicative of the desired weight of the fluid in the reservoir, as a function of time and thereby indicative of the desired rate of flow of fluid from the reservoir, such second signal hereinafter called the "weight reference signal";

a first comparator, having two inputs, on one of which is impressed the weight measurement signal and on another of which is impressed the weight reference signal, and also having an output indicative of the dissimilarity between the weight measurement and weight reference signals;

third means, for controlling flow of the fluid from the reservoir at a rate dependent upon an electrical input thereto, such input being connected so as to receive a signal related to that present at the first comparator's output;

fourth means, placed in the line of flow from the reservoir, (i) for determining the rate at which the drops in the drip chamber are flowing, and (ii) for producing a third electrical signal approximately indicative of the rate of fluid flow, such third signal hereinafter called the "actual drop rate signal";

fifth means, for generating a fourth electrical signal indicative of the desired actual drop rate signal, such fourth signal hereinafter called the "programmed drop rate signal;"

sixth means, having one input on which is placed the programmed drop rate signal and another input to which is connected the output from the first comparator, for modifying the programmed drop rate signal in response to an error correction signal input from the output of the first comparator, so as to produce at an output a fifth electrical signal hereinafter called the "corrected drop rate signal";

a second comparator, having two inputs, on one of which is impressed the actual drop rate signal and on the other one of which is impressed the corrected drop rate signal, and also having an output indicative of the dissimilarity between the actual drop rate signal and the corrected drop rate signal, such output connected to the electrical input of the third means;

whereby the fluid flow rate is directly controlled by the dissimilarity between the drop rate measured by the fourth means and the drop rate specified by the sixth means, and the drop rate specified by the sixth means is corrected by the first comparator's output, so that the flow rate of the fluid is ultimately controlled by the second means.

* * * * *